(12) United States Patent
Jacotot

(10) Patent No.: US 10,961,219 B2
(45) Date of Patent: Mar. 30, 2021

(54) DERIVATIVES AND THEIR USE AS SELECTIVE INHIBITORS OF CASPASE-2

(71) Applicants: INSTITUT NATIONAL DE LA SANTE ET DE LA RECHERCHE MEDICALE (INSERM), Paris (FR); UNIVERSITE PARIS DIDEROT-PARIS 7, Paris (FR)

(72) Inventor: Etienne Jacotot, Paris (FR)

(73) Assignees: INSTITUT NATIONAL DE LA SANTE ET DE LA RECHERCHE MEDICALE (INSERM), Paris (FR); UNIVERSITE PARIS DIDEROT-PARIS 7, Paris (FR)

( * ) Notice: Subject to any disclaimer, the term of this patent is extended or adjusted under 35 U.S.C. 154(b) by 0 days.

(21) Appl. No.: 16/087,346

(22) PCT Filed: Mar. 21, 2017

(86) PCT No.: PCT/EP2017/056696
§ 371 (c)(1),
(2) Date: Sep. 21, 2018

(87) PCT Pub. No.: WO2017/162674
PCT Pub. Date: Sep. 28, 2017

(65) Prior Publication Data
US 2019/0100508 A1 Apr. 4, 2019

(30) Foreign Application Priority Data
Mar. 22, 2016 (EP) .................... 16305318

(51) Int. Cl.
| | |
|---|---|
| *C07D 401/12* | (2006.01) |
| *A61P 27/02* | (2006.01) |
| *A61P 9/10* | (2006.01) |
| *A61P 25/28* | (2006.01) |
| *A61P 1/16* | (2006.01) |
| *A61P 3/04* | (2006.01) |
| *A61P 17/00* | (2006.01) |
| *A61P 29/00* | (2006.01) |
| *C07D 417/14* | (2006.01) |

(52) U.S. Cl.
CPC .............. *C07D 401/12* (2013.01); *A61P 1/16* (2018.01); *A61P 3/04* (2018.01); *A61P 9/10* (2018.01); *A61P 17/00* (2018.01); *A61P 25/28* (2018.01); *A61P 27/02* (2018.01); *A61P 29/00* (2018.01); *C07D 417/14* (2013.01)

(58) Field of Classification Search
CPC ................ C07D 401/12; C07D 417/14; A61K 31/4725; A61P 25/28; A61P 29/00
See application file for complete search history.

(56) References Cited

U.S. PATENT DOCUMENTS 9,133,104 B2 * 9/2015 Davidson .............. C07C 259/06

FOREIGN PATENT DOCUMENTS

| | | | |
|---|---|---|---|
| EP | 2670774 | A1 | 12/2013 |
| WO | 2005/105829 | A2 | 11/2005 |
| WO | 2010065800 | * | 6/2010 |
| WO | 2012/104224 | A1 | 8/2012 |
| WO | 2014/026882 | A1 | 2/2014 |
| WO | 2014026882 | * | 2/2014 |
| WO | 2016/112961 | A1 | 7/2016 |

OTHER PUBLICATIONS

Tu, Nature Cell Biology, vol. 8(1), 72-77, 2006. (Year: 2006).*
Agostini, Biochemical and Biophysical Res COmm, 414, 451-455, 2011. (Year: 2011).*
Baptiste-Okoh, PNAS, vol. 105(6), 1937-1942, 2008. (Year: 2008).*
Gurtu, Analytical Biochemistry, vol. 251, 98-102, 1997. (Year: 1997).*
Lin, J Biomed Optics, vol. 11(2), 024011-1-024011-6, 2006. (Year: 2006).*
ScienceDaily, Sep. 9, 2016, pp. 1-4, <www.sciencedaily.com/releases/2016/09/160909130519.htm>. (Year: 2016).*
Machado, Nature, Feb. 2016, e2096; pp. 1-12. (Year: 2016).*
European Search report for corresponding European Application No. EP 16 30 5318 dated Jun. 6, 2016.
International Search Report for corresponding International Application No. PCT/EP2017/056696 dated May 11, 2017.
Written Opinion for corresponding International Application No. PCT/EP2017/056696 dated May 11, 2017.

(Continued)

*Primary Examiner* — D Margaret M Seaman
(74) *Attorney, Agent, or Firm* — Pearne & Gordon LLP

(57) ABSTRACT

The present invention relates to a compound of formula (I) wherein $P_1$, $P_3$, $P_4$ and $P_5$ are amino acid residues. The invention also relates to a compound of formula (I) for its use as a Caspase-2 inhibitor and for its therapeutical use. It also concerns the use of a compound of formula (I) as activity base probe to selectively detect Caspase-2 activity.

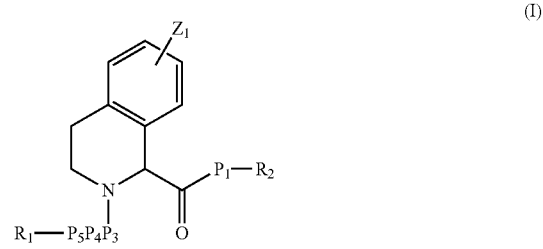

(I)

23 Claims, 1 Drawing Sheet

(56) References Cited

OTHER PUBLICATIONS

Carlsson et al., "Genetic Inhibition of Caspase-2 Reduces Hypoxic-Ischemic and Excitotoxic Neonatal Brain Injury", American Neurological Association, 2011, pp. 781-789 (cited on p. 2).
Ahmed et al., "Ocular neuroprotection by siRNA targeting caspase-2", Cell Death and Disease, 2011, 2, e173, doi:10.1038/cddis.2011.54 (cited on p. 2).
Troy et al., "Caspase-2 Mediates Neuronal Cell Death Induced by β-Amyloid", The Journal of Neuroscience, Feb. 15, 2000, 20(4), pp. 1386-1392 (cited on p. 2).
Ribe et al., "Neuronal caspase 2 activity and function requires RAIDD, but not PIDD", Biochem J., 2012, 444, pp. 591-599 (cited on p. 2).
Pozueta et al., "Caspase-2 is required for dendritic spine and behavioural alterations in J20 APP transgenic mice", Nature Communications, 2013, 4:1939 (cited on p. 2).
Machado et al., "Caspase-2 promotes obesity, the metabolic syndrome and nonalchoholic fatty liver disease", Cell Death and Disease, 2016, 7, e2096; doi:10.1038/cddis.2016.19 (cited on p. 3).
Poreba et al., "Small Molecule Active Site Directed Tools for Studying Human Caspases", Chem Rev., Nov. 25, 2015;115(22)12546-629 (cited on p. 3).
Maillard et al., "Exploiting differences in caspase-2 and -3 S2 subsites for selectivity: Structure-based design, solid-phase synthesis and in vitro activity of novel substrate-based caspase-2 inhibitors", Bioorganic & Medicinal Chemistry, 19, 2011, pp. 5833-5851 (cited on p. 4).
Chauvier et al., "Targeting neonatal ischemic brain injury with a pentapeptide-based irreversible caspase inhibitor", Cell Death and Disease, 2011, 2, e203, doi:10.1038/cddis.2011.87 (cited on p. 17).
Peyrin JM et al. Axon diodes for the reconstruction of oriented neuronal networks in microfluidic chambers. Lab Chip. Nov. 7, 2011;11(21):3663-73.
Deleglise B et al. β-amyloid induces a dying-back process and remote trans-synaptic alterations in a microfluidic-based reconstructed neuronal network. Acta Neuropathol Commun. Sep. 25, 2014;2:145.
Stine WB et al. In vitro characterization of conditions for amyloid-beta peptide oligomerization and fibrillogenesis. J Biol Chem. Mar. 28, 2003;278(13):11612-22.
Shao, Z.-H et al. (2011). Blockade of Caspase-2 Activity Inhibits Ischemia/ Reperfusion-Induced Mitochondrial Reactive Oxygen Burst and Cell Death in Cardiomyocytes. Journal of Cell Death. 2011. 7-18. 10.4137/JCD.S6723.
Technical Notes, Bachem, "Chromophores/Fluorophores: Spectral Properties and Characteristics".
Troy et al., "Nedd2 Is Requried for Apoptosis after Trophic Factor Withdrawal, But Not Superoxide Dismutaase (SOD1) Downregulation, in Sympathetic Neurons and PC12 Cells", The Journal of Neuroscience, Mar. 15, 1997, 17(6), pp. 1911-1918.
Stefanis et al., "Caspase-2 (Nedd-2) Processing and Death of Trophic Factor-Deprived PC12 Cells and Sympathetic Neurons Occur Independently of Caspase-3 (CPP32)-Like Activity", The Journal of Neuroscience, Nov. 15, 1998, 18(22), pp. 9204-9215.
Troy et al., "Death in the Balance: Alternative Participation of the Caspase-2 and -9 Pathways in Neuronal Death Induced by Nerve Growth Factor Deprivation", The Journal of Neuroscience, Jul. 15, 2001, 21(14), pp. 5007-5016.
Chauvier et al., "Upstream control of apoptosis by caspase-2 in serum-deprived primary neurons", Apoptosis, vol. 10, Oct. 3, 2005, pp. 1243-1259.
Carlsson et al., "Genetic Inhibition of Caspase-2 Reduces Hypoxic-Ischemic and Excitotoxic Neonatal Brain Injury", American Neurological Association, 2011.
Niizuma et al., "the PIDDosome mediates delayed death of hippocampal CA1 neurons after transient global cerebral ischemia in rats", PNAS, Oct. 21, 2008, vol. 105, No. 42, pp. 16368-16373.
Troy et al., "Caspase-2 Mediates Neuronal Cell Death Induced by β-Amyloid", The Journal of Neuroscience, Feb. 15, 2000, 20(4), pp. 1386-1392.
Troy et al., "β-Amyloid-induced neuronal apoptosis requires c-Jun N-terminal kinase activation", Journal of Neurochemistry, 2001, 77, pp. 157-164.
Pozueta et al., "Caspase-2 is required for dendritic spine and behavioural alterations in J20 APP transgenic mice", Nature Communications, Published Jun. 10, 2013, 4:1939.
Zhao et al., "Caspase-2 cleavage of tau reversibly impairs memory", Nature Medicine, Published Oct. 10, 2016, 10.1038.
Liu et al., "A soluble truncated tau species related to cognitive dysfunction is elevated in the brain of cognitively impaired human individuals", Scientific Reports, Nature Research, 2020, 10:3869.
Smith et al., "A soluble tau fragment generated by caspase-2 is associated with dementia in Lewy body disease", Acta Neuropathologica Communications, 2019, 7:124.
Tiwari et al., "A knockout of the caspase 2 gene produces increased resistance of the nigrostriatal dopaminergic pathway to MPTP-induced toxicity", National Institutes of Health, Jun. 2011, 229(2), pp. 421-428.
Liu et al., "A soluble truncated tau species related to cognitive dysfunction and caspase-2 is elevated in the brain of Huntington's disease patients", Acta Neuropathologica Communications, 2019, 7:111.
Carroll et al., "Mice lacking caspase-2 are protected from behavioral changes, but not pathology, in the YAC128 model of Huntington disease", Molecular Degeneration, 2011, 6:59.
Chauvier et al., "Targeting neonatal ischemic brain injury with a pentapeptide-based irreversible caspase inhibitor", Cell Death and Disease, 2011, 2, e203.
Sifringer et al., "Prevention of neonatal oxygen-induced brain damage by reduction of intrinsic apoptosis", Cell Death and Disease, 2012, 3, e250.
Carlsson et al., "Combined effect of hypothermia and caspase-2 gene deficiency on neonatal hypoxic-ischemic brain injury", Pediatric Research, Published Mar. 7, 2012, 10:1038.
Ahmed et al., "Ocular neuroprotection by siRNA targeting caspase-2", Cell Death and Disease, 2011, 2, e173.
Vigneswara et al., "Pharmacological Inhibition of Caspase-2 Protects Axotomised Retinal Ganglion Cells from Apoptosis in Adult Rats", Plos One, Dec. 2012, vol. 7, Issue 12.
Vigneswara et al., "Long-term neuroprotection of retinal ganglion cells by inhibiting caspase-2", Cell Death Discovery, 2016, 2, 16044.
Thomas et al., "Caspase-2 Mediates Site-Specific Retinal Ganglion Cell Death After Blunt Ocular Injury", Retinal Cell Biology, ISSN: 1552-5783; Downloaded from iovs.arvojournals.org on Jul. 15, 2020.
Vigneswara et al., "Pigment epithelium-derived factor mediates retinal ganglion cell neuroprotection by suppression of caspase-2", Cell Death & Disease, 2019, 10:102.
Bronner et al., "Endoplasmic Reticulum Stress Activates the Inflammasome via NLRP3-and Caspase-2-Driven Mitochondrial Damage", Immunity 43, Sep. 15, 2015, pp. 415-462.
Ferreira et al., "Apoptosis and insulin resistance in liver and peripheral tissues of morbidly obese patients is associated with different stages of non-alcoholic fatty liver disease", Diabetologia, 2011, 54, pp. 1788-1798.
Ivey et al., "Additive effects of nicotine and high-fat diet on hepatocellular apoptosis in mince: Involvement of caspase-2 and inducible nitric oxide synthase-mediated intrinsic pathway signaling".
Machado et al., "Reduced Lipoapoptosis, Hedgehog Pathway Activation, and Fibrosis in Caspase-2 deficient Mice with Nonalcoholic Steatophepatitis", Gut. Jul. 2015, 64(7), pp. 1148-1157.
Machado et al., "Caspase-2 promotes obesity, the metabolic syndrome and nonalcoholic fatty liver disease", Cell Death and Disease, 2016 7, e2096.
Machado et al., "Vitamin B5 and N-acetylcysteine in nonalcoholic steatohepatitis: a pre-clinical study in a dietary mouse model", Dig Dis Sci, Jan. 2016, 61(1), pp. 137-148.
Wilson et al., "Caspase-2 deficiency enhances whole-body carbohydrate utilisation and prevents high-fat diet-induced obesity", Cell Death and Disease, 2017, 8, e3136.

(56) References Cited

OTHER PUBLICATIONS

Kim et al., "ER Stress Drives Lipogenesis and Steatohepatitis via Caspase-2 Activation of S1P", Cell 175, Sep. 20, 2018, pp. 133-145.
Dorstyn et al., "An unexpected role for caspase-2 in neuroblastoma", Cell Death and Disease, 2014, 5, e1383.

* cited by examiner

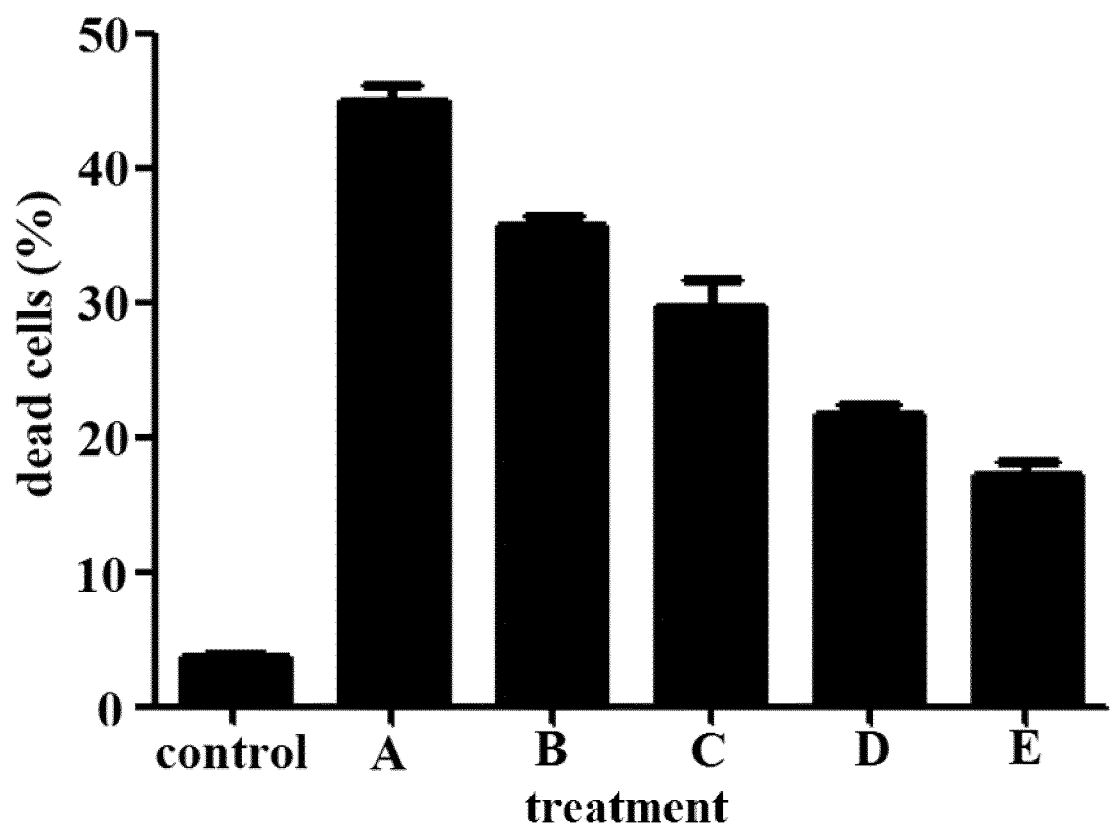

DERIVATIVES AND THEIR USE AS SELECTIVE INHIBITORS OF CASPASE-2

The present invention relates to novel compounds which are useful as selective inhibitors of Caspase-2. This invention also relates to the therapeutic use of these compounds and to their use as activity based probes (ABPs) for Caspase-2.

Caspases are a family of intracellular endoproteases using a cysteine residue at the initiation of the cleavage of peptide substrates. They are widely known to have important implications in the regulation of inflammation as well as a crucial role in the control of programmed cell death by apoptosis.

Caspases are classified in two major groups: those involved in the regulation of inflammatory processes (-1, -4, -5, -11, -12) and those that are central to the initiation and execution of apoptosis. There are two groups among apoptotic Caspases, the "initiators" who have a long N-terminal pro-domain (Caspase-2, -8, -9, -10), and those with a short pro-domain (residues 20-30) who are the "executors" of apoptosis (Caspase-3, -6, -7). Caspases involved in inflammation and the initiation of apoptosis have structural units involved in the transduction of the apoptotic signal, such as "Death Effector Domain" (DED) and "Caspase Recruitment Domain" (CARD). Each of these domains allows homotypic interaction with other protein partners.

The enzymatic properties of Caspases are governed by the existence of a catalytic dyad (cysteine, histidine) where cysteine acts as a nucleophile for the initiation of cleavage of peptide bonds. The active site of Caspases is highly conserved, with the catalytic cysteine included in a peptide sequence QACXG (where X is arginine (R), glutamine (Q) or glycine (G)) and a basic subsite S1, which gives them specificity for substrate cleavage after an aspartate residue, which is unique among mammalian proteases, except for the serine protease granzyme B. Generally, Caspases recognize a tetra-peptide motif, P1-P4 in N-ter of the cleavable bond, respectively recognized by subsites S1-S4 of the enzyme. The downstream positions Aspartate (P'1 and P'2) are also involved in the recognition and specificity vis-à-vis of Caspases.

Caspases have been classified in three groups based on the substrate peptide sequences they preferentially recognize. Group I Caspases (-1, -4 and -5) have a preference for a hydrophobic residue in P4. While the enzymes of group II (-2, -3, -7) have a strong preference for an Aspartate at this position, Group III (-6, -8, -9, -10) favors small aliphatic chains P4. In the group II, Caspase-2 has a unique recognition modality; indeed, it requires the recognition of a residue at position P5 (preferably a leucine, isoleucine, valine, or alanine) to exert its catalytic activity. Caspase-3 and -7 also recognize a P5 residue in a non-obligatory way.

Originally named Nedd-2, "Neural precursor cell Expressed developmentally down-regulated 2" in mice and Ich-1, "ICE and CED3 homolog" in humans, Caspase-2, encoded by the gene CASP2 (chr. 7q34-q35), is the most conserved member of this family of enzymes. Its activity is finely regulated during neuronal development in humans. There are two isoforms of the Caspase-2 isoform proapoptotic 2L and 2S isoform (truncated) antiapoptotic. 2L isoform is the predominant form in most tissues, but 2S isoform is expressed at similar levels in brain, skeletal muscle and heart.

Caspase-2 acts as an initiator Caspase that poorly cleaves other Caspases but can initiate mitochondrial outer membrane permeabilization, and that regulates diverse stress-induced signaling pathways including heat shock, DNA damage, mitochondria oxidative stress, and cytoskeleton disruption.

Beside apoptosis, Caspase-2 participates in the regulation of oxidative stress. For instance, elderly Casp-$2^{-/-}$ mice show reduced Superoxyde Dismutase and Gluthation peroxydase activities. In some specific circumstances, Caspase-2 can act as a tumor suppressor. Indeed, under oncogenic stress (as in the Eµ-Myc transgenic mouse model), Caspase-2 deficiency potentiates tumorigenesis. Recent data also suggest that Caspase-2 might inhibit autophagy.

Genetic inhibition of Caspase-2 was found to be neuroprotective in newborn mice exposed to hypoxic-ischemic or excitotoxic challenges, suggesting that Caspase-2-mediated cell death might contribute to the pathophysiology of perinatal brain injury (Carlsson et al., Annals of Neurology 2011, 70(5):781-9). In addition, genetic inhibition of Caspase-2 confers ocular neuroprotection (Amhed Z et al., Cell Death Dis. 2011 Jun. 16; 2:e173).

In cellular models of Alzheimer's disease (Carol M. Troy et al. The Journal of Neuroscience, Feb. 15, 2000, 20(4): 1386-1392), Caspase-2 is a key effector of neuronal death induced by the amyloid peptide Aβ (Ribe E M et al., Biochem J. 2012 444(3):591-9).

Moreover, using amyloid precursor protein transgenic mice, Pozueta et al. (Nat Commun. 2013; 4:1939) have shown that:

(i) Caspase-2 is required for the cognitive decline in this Alzheimer animal model, (ii) cultured hippocampal neurons lacking Caspase-2 are immune to the synaptotoxic effects of Aβ, and (iii) Caspase-2 is a critical mediator in the activation of the RhoA/ROCK-II signaling pathway, leading to the collapse of dendritic spines, thus suggesting that Caspase-2 is a key driver of synaptic dysfunction in Alzheimer's disease.

Caspase-2 also appears to promote obesity, metabolic syndrome and nonalcoholic fatty liver disease. Indeed, it has been shown that Caspase-2 deficient mice were protected from these conditions (Machado M V et al. Cell Death Dis. 2016 Feb. 18; 7:e2096).

The first generations of Caspases inhibitors were aldehyde peptides which reversibly inhibit Caspases. Several sequences supposedly confer preferential effects vis-à-vis some members of the Caspase family have been developed including Ac-DEVD-CHO (a preferential inhibitor of Caspase-3 and Caspase-7) and Ac-VDVAD-CHO (a preferential inhibitor of Caspase-2, -3, and -7).

In the second generation of Caspases inhibitors, the aldehyde group has been replaced by α-substituted ketones with a fluoromethyl ketone group (fmk). This type of inhibitor inactives the enzyme by forming an adduct with the active site cysteine. Z (Benzyloxylcarbonyle)-VAD-fmk is a broad spectrum inhibitor of this generation. These molecules are toxic in vivo, because the release of fluoroacetate group, particularly in the liver, leads to the inhibition of aconitase. Thus, the development of inhibitors with a fmk group, was abandoned in the preclinical phase because of its hepatotoxicity. Then, several Caspase inhibitors have been synthetized in the art (Poreba et al., Chem Rev. 2015 Nov. 25; 115(22):12546-629). In particular, compounds able to inhibit Caspase-2 activity have been reported for example in WO 2005/105829 and EP2670774. However, these known Caspase-2 inhibitors also have a too high activity with respect to Caspase-3. They thus cannot be qualified as selective Caspase-2 inhibitors.

More recently, a series of reversible Caspase-2 inhibitor has been reported. When evaluated in vitro on human recombinant Caspases, these compounds were found to preferentially inhibit Caspase-2, but have moderate effects in cellular assays and structural properties that are incompatible with in vivo use (Maillard et al., Biorganic & Medicinal Chemistry 19 (2011) 5833-5851).

Accordingly, there is still a need for potent and selective Caspase-2 inhibitors more particularly with a significantly reduced activity against Caspase-3. In particular, it would be highly advantageous to provide more selective and efficient Caspase-2 inhibitors for use in the prevention and/or treatment of diseases and/or injuries in which Caspase-2 activity is implicated such as neonatal brain ischemia, heart ischemia and chronic degenerative diseases like for instance Alzheimer's disease.

It would also be very advantageous to provide more efficacious and selective Caspase-2 inhibitors for use as an activity-based probe to specifically detect Caspase-2 activity.

The compounds of the invention aim to meet these needs.

Thus, according to one of its aspects, the present invention relates to a compound of formula (I):

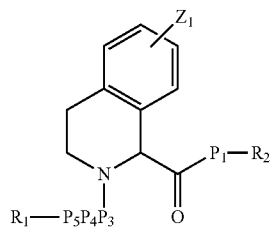

wherein:
$Z_1$ is a $(C_1-C_6)$alkyl group;
$P_5$ is selected from the following amino acid residues

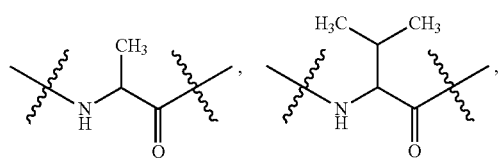

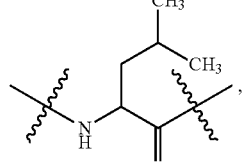

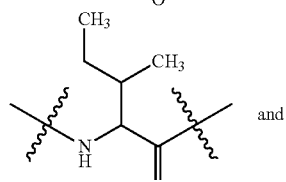

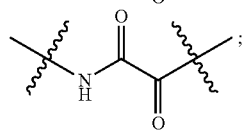

$P_1$ and $P_4$, identical or different, are selected from the following amino acid residues

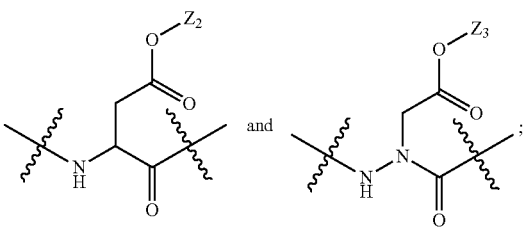

in which $Z_2$ and $Z_3$, identical or different, are selected from a hydrogen atom and a $(C_1-C_6)$alkyl group;

$P_3$ is selected from the following amino acid residues

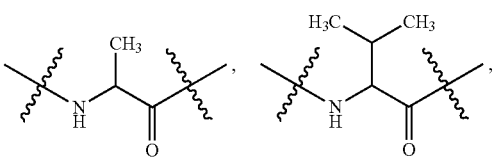

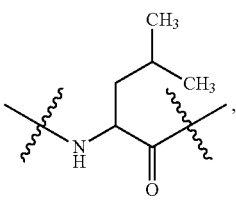

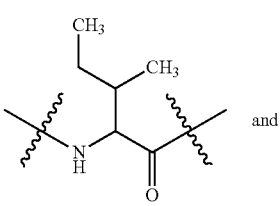

$R_1$ is selected from

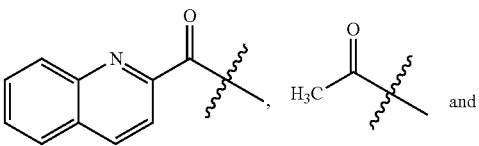

-continued

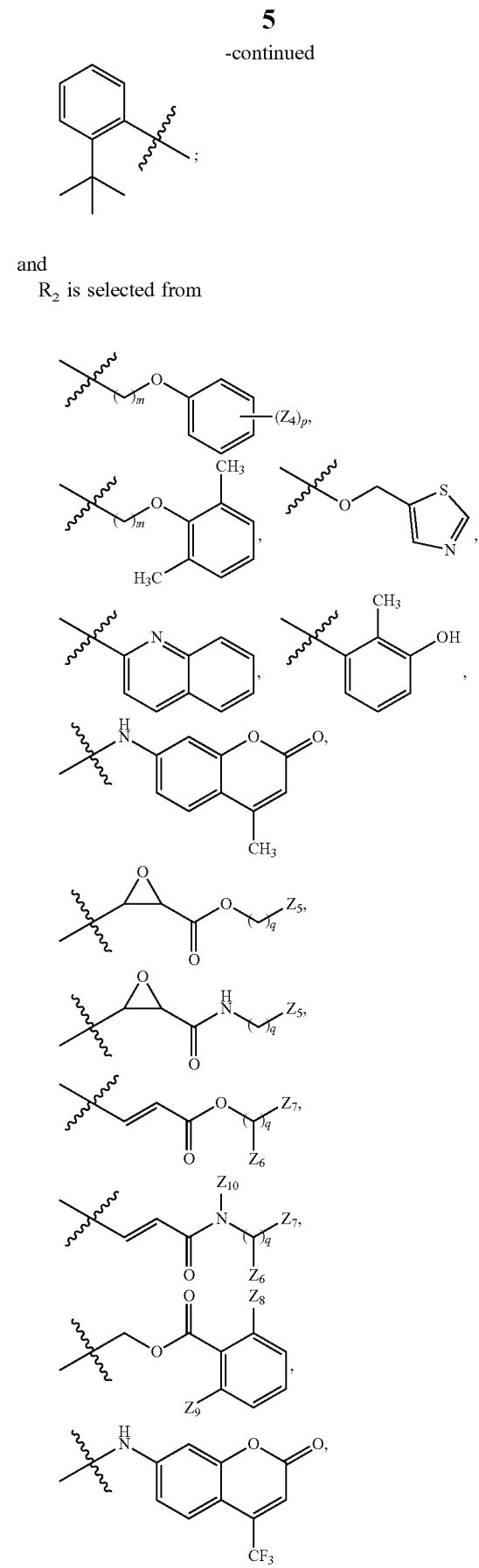

and
R$_2$ is selected from

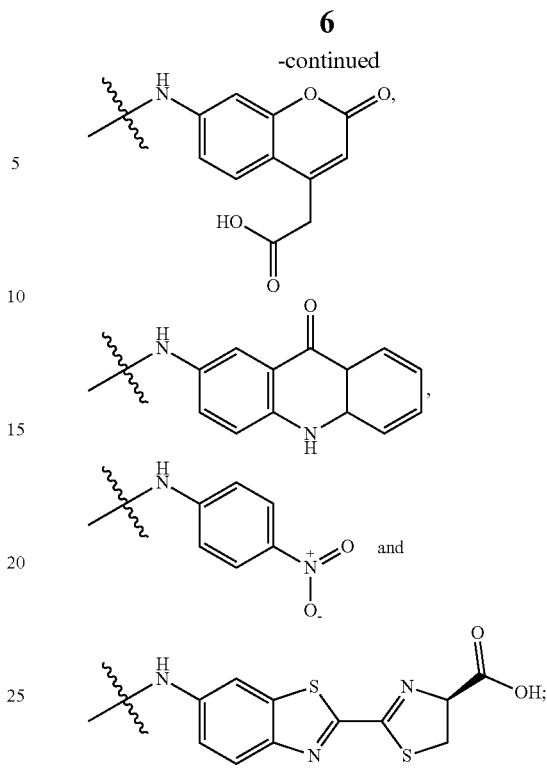

in which
m is 0, 1 or 2;
p is 1, 2, 3 or 4;
Z$_4$ is a halogen atom;
q is 0 or 1;
Z$_5$ is selected from a (C$_1$-C$_6$)alkyl and a phenyl group, said phenyl group being optionally substituted by an amino group;
Z$_6$, Z$_7$ and Z$_{10}$, identical or different, are selected from a hydrogen atom, a (C$_1$-C$_4$)alkyl, a tetrahydroquinolynyl and a —(CH$_2$)$_i$-aryl group with i being 0, 1 or 2, said aryl group being optionally substituted by one, two, three, or four halogen atom(s) or one (C$_1$-C$_4$) alkyl group; and
Z$_8$ and Z$_9$, identical or different, are selected from a halogen atom and a (C$_1$-C$_6$)alkyl group;
or one of its salts;
said compound of formula (I) being in all the possible racemic, enantiomeric and diastereoisomeric isomer forms.

After extensive research, the inventor has found that these compounds of formula (I) acts as selective and effective inhibitors of Caspase-2 activity as demonstrated in the following examples.

Indeed, the compounds of the present invention are much more efficient to inhibit Caspase-2 than to inhibit Caspase-3.

In particular, as shown in the following examples, some compounds of the invention exhibit an inhibitory effect on Caspase-2 at least two times, preferably at least 5 times, more preferably at least 10 times, and even more preferably at least 15 times higher than their inhibitory effect on Caspase-3.

The inhibitory effect of the compounds of the invention with respect to Caspase-2 and Caspase-3 may be evaluated by kinetic approaches using human recombinant Caspases. For irreversible inhibitors, k$_{inact}$/K$_I$ ratio is determined using the method disclosed in example 2. For reversible inhibitors k$_i$ is determined.

Moreover, the fact that some of these inhibitors are irreversible is very advantageous since this type of inhibitors can be used in prolonged suppression of Caspase-2, limited only by the normal rate of protein resynthesis, also called turnover.

In the meaning of the present invention:

A "Caspase inhibitor" is intended to mean a compound that reduces or suppresses the activity of the targeted Caspase, as compared with said activity determined without said inhibitor.

A "selective Caspase-2 inhibitor" is intended to mean a compound that decreases the activity of Caspase-2 more than the activity of other Caspases, in particular Caspase-3.

Thus, according to a second aspect, the invention is directed to a compound of the invention for its use as selective Caspase-2 inhibitor.

According to one embodiment, the $R_2$ radical of the compounds of the invention is selected from

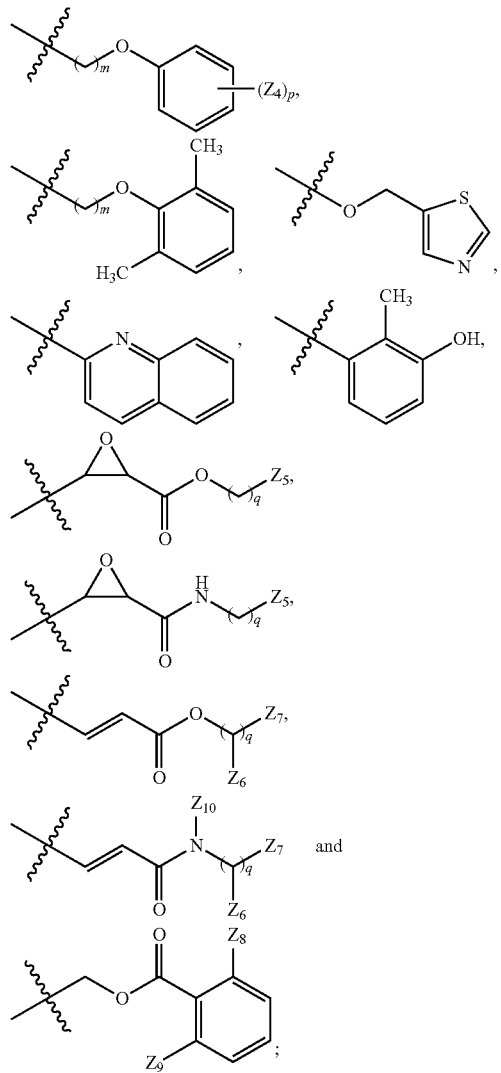

in which m, p, q, $Z_4$, $Z_5$, $Z_6$, $Z_7$, $Z_8$, $Z_9$ and $Z_{10}$ are as above defined.

These compounds may advantageously be introduced in a pharmaceutical composition. These compounds may be used as a medicament. More particularly, they may be used in the prevention and/or treatment of diseases and/or injuries in which Caspase-2 activity is implicated.

For the purposes of the present invention the term "prevention" means at least partly reducing the risk of manifestation of a given phenomenon, i.e., in the present invention, a disease and/or injurie in which Caspase-2 activity is implicated. A partial reduction implies that the risk remains, but to a lesser extent than before implementing the invention.

For the purposes of the present invention the term "treatment" is intended to mean completely or partially curing a given phenomenon, i.e., in the present invention, a disease and/or injurie in which Caspase-2 activity is implicated, including decreasing, minimizing or reducing said given phenomenon.

Thus, according to a third aspect, the invention is directed to a pharmaceutical composition comprising at least one compound of the invention wherein $R_2$ is as above defined and at least one pharmaceutically acceptable excipient.

According to a fourth aspect, the invention is directed to a compound of the invention wherein $R_2$ is as above defined, for its use as a medicament.

According to a fifth aspect, the invention is directed to a compound of the invention wherein $R_2$ is as above defined, for its use in the prevention and/or treatment of diseases and/or injuries in which Caspase-2 activity is implicated.

According to another embodiment, the $R_2$ radical of the compounds of the invention is selected from

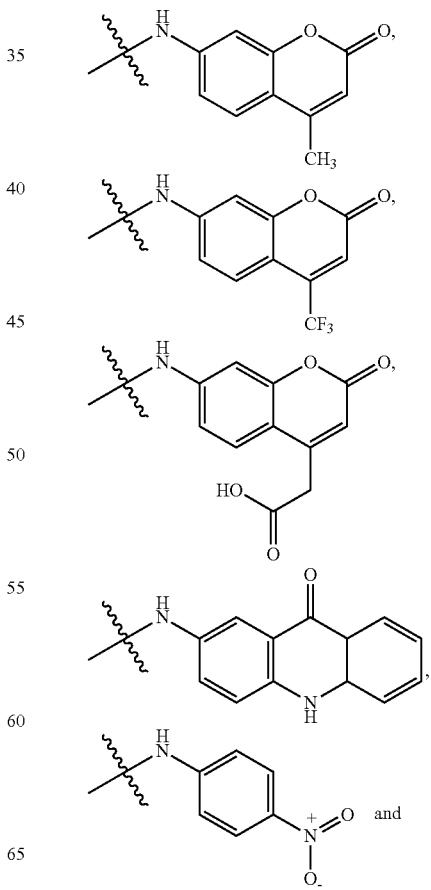

-continued

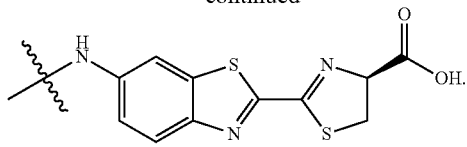

These compounds may advantageously be used as an activity-based probe to selectively detect Caspase-2 activity.

Thus, according to a sixth aspect, the invention is directed to the use of a compound of the invention wherein $R_2$ is as above defined, as an activity-based probe to selectively detect Caspase-2 activity.

In the context of the present invention, the following abbreviations and empirical formulae are used:

Boc Tert-Butyloxycarbonyl
° C. Degree Celsius
Me Methyl
Bn Benzyl
AMC 7-amino-4-methylcoumarin
PBS Phosphate Buffered Saline
Ac Acetyl
RFU Relative Fluorescence Units
HEPES 4-(2-hydroxyethyl)-1-piperazineethanesulfonic acid
DTT Dithiothreitol
EDTA Ethylenediaminetetraacetic acid
CHAPS (3-((3-cholamidopropyl) dimethylammonio)-1-propanesulfonate)
DMSO Dimethyl sulfoxide In keeping with standard polypeptide nomenclature (J. Biol. Chem., 243:3552-59 (1969)) abbreviations for amino acid residues used in the present invention are as follows:

A Alanine
V Valine
D Aspartic acid
E Glutamic acid

It should further be noted that in all amino-acid residue sequences that are represented in the present invention by using the above mentioned abbreviations, the left and right orientation is in the conventional direction of amino-terminus to carboxy-terminus.

Accordingly, it appears clearly that in a formula defining a peptide according to the invention, when a sequence of amino acids such as R1-P5P4P3- or -P1-R2 is indicated:

(i) the

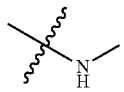

part of the P5 amino acid residue is linked to R1;
the one of the P4 amino acid residue is linked to the P5 amino acid residue;
the one of the P3 amino acid residue is linked to the P4 amino acid residue; and
the one of the P1 amino acid residue is linked to

at the opposite of R2 as represented in formula (I); and
(ii) the

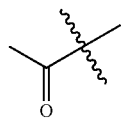 [SMILES: *C(C)=O]

part of the P5 amino acid residue is linked to the P4 amino acid residue;
the one of the P4 amino acid residue is linked to the P3 amino acid residue;
the one of the P3 amino acid residue is linked to the

at the opposite of the P4 amino acid residue as represented in formula (I); and
the one of the P1 amino acid residue is linked to R2.

Other features and advantages of the invention will emerge more clearly from the description, the examples which follow given by way of non-limiting illustration, and from the FIG. 1.

FIG. 1 represents a graph that gives the percentage of dead cells depending on the treatment applied to the tested cells (situations A to E wherein vinctistine is either applied alone (20 nM) to the cells (situation A) or in combination with various quantities of compound 2 according to the invention (respectively 3, 10, 30 and 60 µM for situations B, C, D and E) and control (no treatment)). (%+S.D.; n=3)

COMPOUNDS OF THE INVENTION

As above-mentioned, the compounds according to the invention correspond to general formula (I):

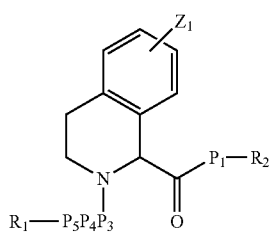

wherein:
$Z_1$ is a $(C_1\text{-}C_6)$alkyl group;
$P_5$ is selected from the following amino acid residues

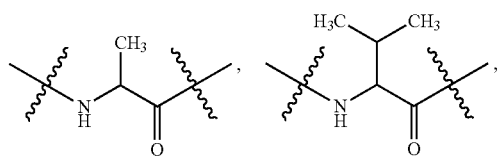

-continued
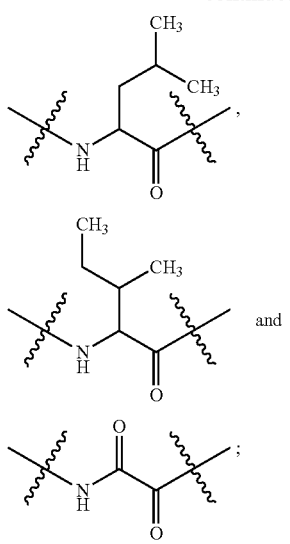
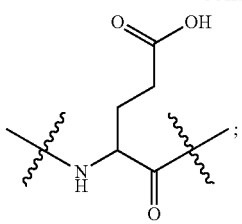
R₁ is selected from
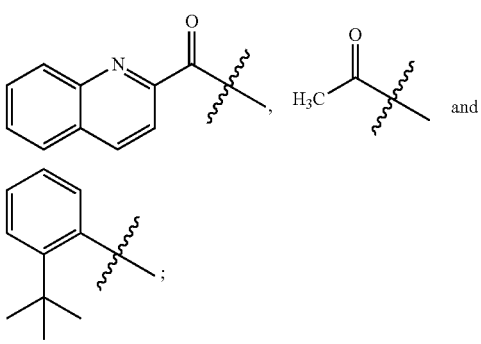
P₁ and P₄, identical or different, are selected from the following amino acid residues
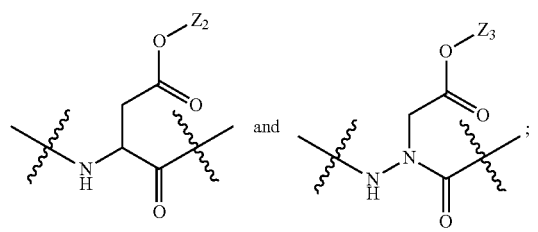
in which $Z_2$ and $Z_3$, identical or different, are selected from a hydrogen atom and a $(C_1-C_6)$alkyl group;
P₃ is selected from the following amino acid residues
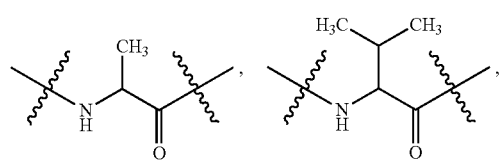
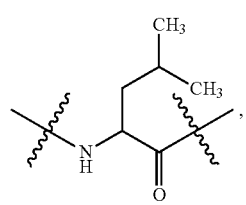
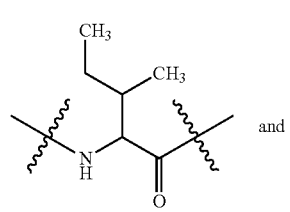
and
R₂ is selected from
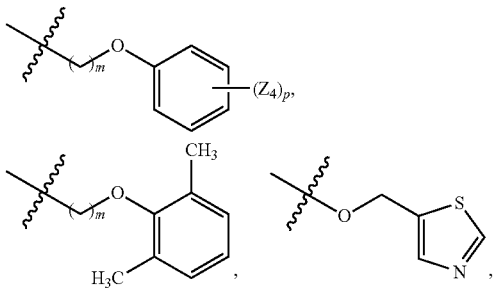
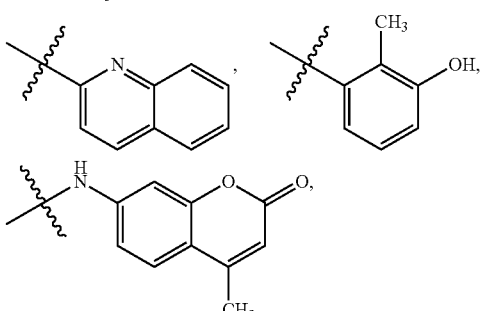
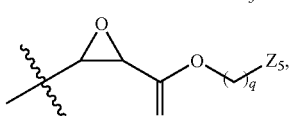
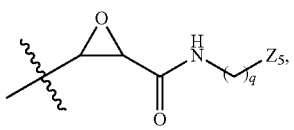

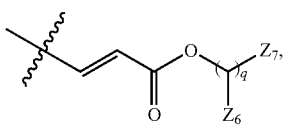
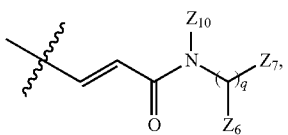
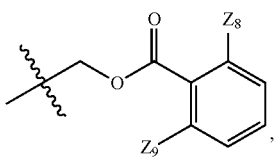
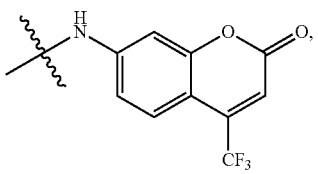
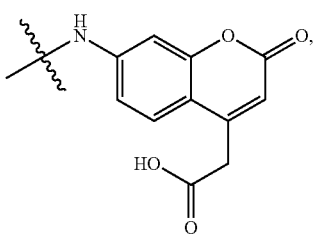
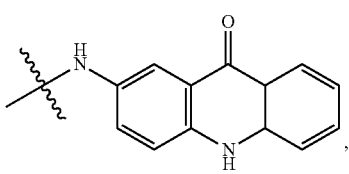
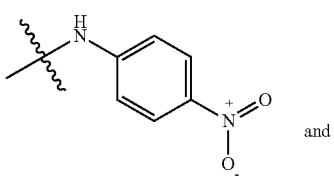
and

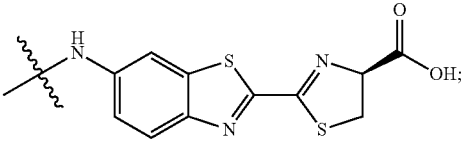

in which m is 0, 1 or 2;
p is 1, 2, 3 or 4;
$Z_4$ is a halogen atom;
q is 0 or 1;
$Z_5$ is selected from a $(C_1-C_6)$alkyl and a phenyl group, said phenyl group being optionally substituted by an amino group;
$Z_6$, $Z_7$ and $Z_{10}$, identical or different, are selected from a hydrogen atom, a $(C_1-C_4)$alkyl, a tetrahydroquinolynyl and a —$(CH_2)_i$-aryl group with i being 0, 1 or 2, said aryl group being optionally substituted by one, two, three, or four halogen atom(s) or one $(C_1-C_4)$ alkyl group; and
$Z_8$ and $Z_9$, identical or different, are selected from a halogen atom and a $(C_1-C_6)$alkyl group;
or one of its salts;
said compound of formula (I) being in all the possible racemic, enantiomeric and diastereoisomeric isomer forms.

Accordingly, the compounds of the invention comprise several asymmetric carbon atoms. They thus may exist in the form of enantiomers or diastereoisomers. These enantiomers and diastereoisomers, and also mixtures thereof, including racemic mixtures, form part of the invention.

The compounds of the invention may also exist in the form of bases or of acid-addition salts. These salts may be prepared with pharmaceutically acceptable acids, but the salts of other acids that are useful, for example, for purifying or isolating the compounds of formula (I) also form part of the invention.

The term "pharmaceutically acceptable" means what is useful in preparing a pharmaceutical composition generally safe, non-toxic, and neither biologically nor otherwise undesirable and includes what is acceptable for veterinary as well as human pharmaceutical use.

The compounds of the invention may also exist in the form of hydrates or solvates, i.e. in the form of associations or combinations with one or more molecules of water or with a solvent. Such hydrates and solvates also form part of the invention.

In the context of the present invention, the following definitions apply:

a halogen atom: a fluorine, a chlorine, a bromine or an iodine atom. The halogen atoms may be more particularly fluorine atoms.

$C_t-C_z$: a carbon-based chain possibly containing from t to z carbon atoms in which t and z may take values from 1 to 10; for example, $C_1-C_3$ is a carbon-based chain possibly containing from 1 to 3 carbon atoms.

an alkyl: a linear or branched saturated aliphatic group, in particular comprising form 1 to 6 carbon atoms. Examples that may be mentioned include methyl, ethyl, n-propyl, isopropyl, butyl, isobutyl, tert-butyl, pentyl, neopenthyl etc. . . .

an alkoxy: a radical —O-alkyl in which the alkyl group is as defined previously.

an aryl: a monocyclic or bicyclic aromatic group containing between 5 and 10 carbon atoms, in particular between 6 and 10 carbon atoms. By way of examples of an aryl group, mention may be made of phenyl or naphthyl group. Preferably, the aryl group is phenyl.

Among the compounds of general formula (I) according to the invention, a subgroup of compounds is constituted by the compounds of formula (II):

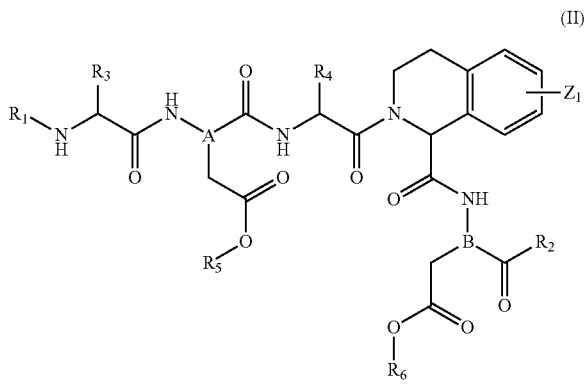

(II)

wherein:

$R_1$, $R_2$ and $Z_1$ are as defined in the formula (I);

$R_3$ is selected from a —$CH_3$, a —$CH(CH_3)_2$, a —$CH_2CH(CH_3)_2$ and a —$CH(CH_3)CH_2CH_3$ group;

A and B, identical or different, are selected from a nitrogen atom and a —CH— group;

$R_5$ and $R_6$, identical or different, are selected from a hydrogen atom and a ($C_1$-$C_6$)alkyl group; and $R_4$ is selected from a —$CH_3$, a —$CH(CH_3)_2$, a —$CH_2CH(CH_3)_2$, a —$CH(CH_3)CH_2CH_3$ and a —$(CH_2)_2CO_2H$ group;

or one of its salts;

said compound of formula (II) being in all the possible racemic, enantiomeric and diastereoisomeric isomer forms.

Preferably in formula (II), at least one of A and B is a —CH group, more preferably, A and B are —CH groups.

According to a preferred mode of the invention, the compounds according to the invention may be of formula (III):

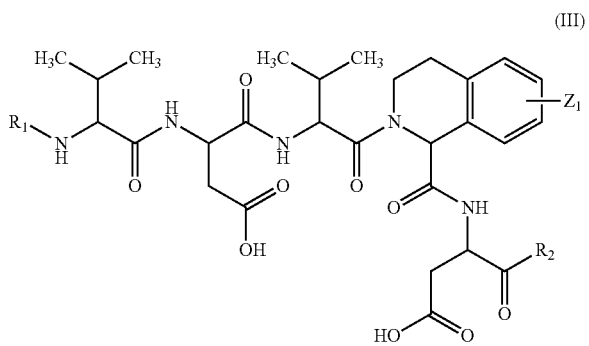

(III)

wherein $R_1$, $R_2$ and $Z_1$ are as defined in the formula (I); or one of its salts;

said compound of formula (III) being in all the possible racemic, enantiomeric and diastereoisomeric isomer forms.

According to a preferred embodiment, the compounds according to the invention may be of formula (IV):

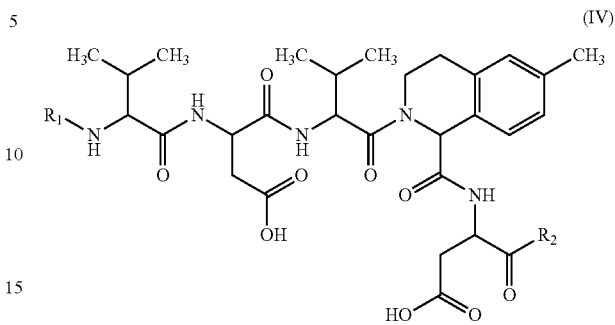

(IV)

wherein $R_1$ and $R_2$ are as defined in the formula (I);

or one of its salts;

said compound of formula (IV) being in all the possible racemic, enantiomeric and diastereoisomeric isomer forms.

According to yet another preferred embodiment, in formula (I), (II), (III) and/or (IV), $R_1$ is

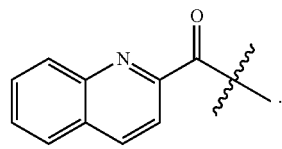 [SMILES: *C(=O)c1ccc2ccccc2n1]

According to another preferred embodiment, in formula (I), (II), (III) and/or (IV), $R_2$ is selected from

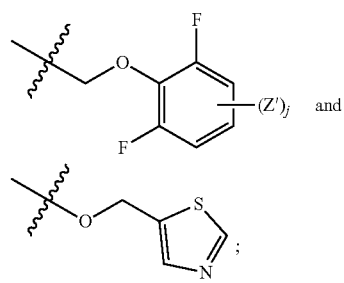

in which Z' is a fluorine atom and j is 0, 1 or 2.

Preferably, $R_2$ is

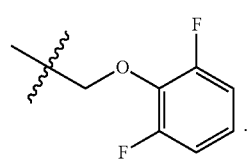 [SMILES: *COc1c(F)cccc1F ; "."]

According to yet a preferred embodiment, the compounds according to the invention have at least one, preferably at least three asymmetric carbon atoms of (S) configuration. More preferably all the asymmetric carbon atoms of the compounds according to the invention are of (S) configuration.

Among the compounds of general formula (I) according to the invention, mention may be made especially of the following compounds:

| STRUCTURE/Compound No | | IUPAC NAME |
|---|---|---|
| [structure] | 1 | (3S)-4-(((2S)-1-(1-(((S)-3-carboxy-1-oxo-1-(thiazol-5-ylmethoxy)propan-2-yl)carbamoyl)-7-methyl-3,4-dihydroisoquinolin-2(1H)-yl)-3-methyl-1-oxobutan-2-yl)amino)-3-((S)-3-methyl-2-(quinoline-2-carboxamido)butanamido)-4-oxobutanoic acid |
| [structure] | 2 | (S)-3-((S)-2-((S)-2-((S)-3-carboxy-2-((S)-3-methyl-2-(quinoline-2-carboxamido)butanamido)propanamido)-3-methylbutanoyl)-6-methyl-1,2,3,4-tetrahydroisoquinoline-1-carboxamido)-5-(2,6-difluorophenoxy)-4-oxopentanoic acid |

Preferably, the compound of general formula (I) is:

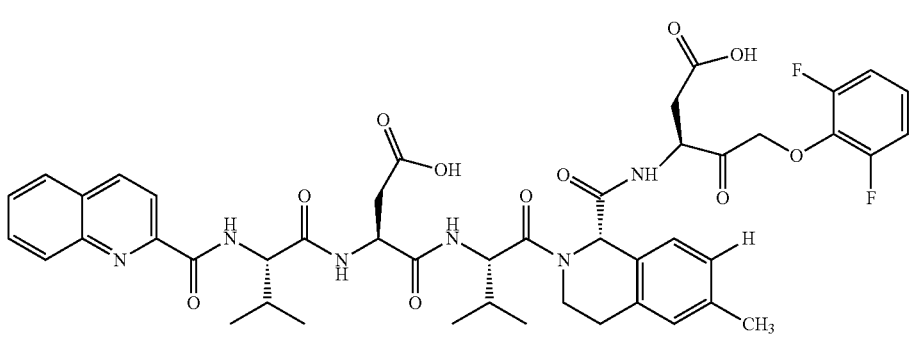

Preparation of the Compounds of the Invention

The compounds of the invention may be prepared by organic and peptide synthesis. Assembly of the structure by peptide synthesis belongs to the general knowledge of the skilled artisan and further details are depicted in Linton et al., J. Med. Chem. 2005, 48, 6779-6782 and in Chauvier et al Cell Death Dis 2011, 2:e203. The precursors of $R_1$, $R_2$, $P_1$, $P_3$, $P_4$ and $P_5$ that lead to the compounds of the invention are introduced in the different steps of the process.

The precursor may either be commercial product or commercial product that has been functionalized according to well-known protocols for the skilled artisan. Further details and references can be made to "Design of Caspase inhibitors as potential clinical agents; CRC press; CRC Enzyme inhibitors series, Edited by Tom O'Brien & Steven D. Linton chapter 7 by BR Ullman.

In particular, example 1 of the present invention illustrates the protocol of preparation of the compound 2 according to the invention.

Applications

As specified previously and clearly illustrated by the following examples, the compounds according to the present invention are useful as selective Caspase-2 inhibitors.

Indeed, as pointed out by the examples they show a much better inhibitory effect for Caspase-2 than for Caspase-3. As a consequence, they are efficient to selectively inhibit Caspase-2 with respect to Caspase-3.

a) Therapeutic Field

In view of the above, the compounds of the present invention, and more particularly the compounds for which the $R_2$ radical is selected from

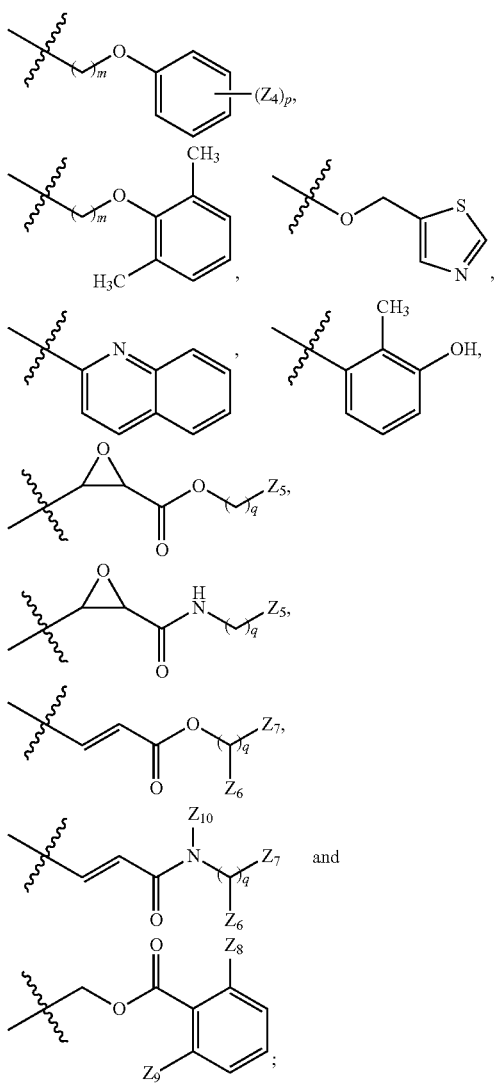

in which m, p, q, $Z_4$, $Z_5$, $Z_6$, $Z_7$, $Z_8$, $Z_9$ and $Z_{10}$ are as above defined,
may be used in the therapeutic field.

According to one of its aspects, the present invention therefore relates to a compound of the invention wherein $R_2$ is as above defined, for its use as a medicament, in particular a medicament intended to selectively inhibit the activity of Caspase-2.

In other terms, the invention concerns the use of a compound according to the invention in which $R_2$ is as above defined for the preparation of a medicine, in particular of a drug for selectively inhibiting the activity of Caspase-2.

In other words, the present invention relates to a medicament comprising at least one compound according to the invention in which $R_2$ is as above defined, in particular a medicament for selectively inhibiting the activity of Caspase-2.

Thus, according to another of its aspects, the invention is directed to a compound of the invention wherein $R_2$ is as above defined, for its use in the prevention and/or treatment of diseases and/or injuries in which Caspase-2 activity is implicated.

In other terms, the invention concerns the use of a compound according to the invention in which $R_2$ is as above defined for the preparation of a medicament intended to prevent and/or treat diseases and/or injuries in which Caspase-2 activity is implicated.

In particular, said diseases and/or injuries may be selected among pathologies with cell death, particularly among:
chronic degenerative diseases such as Alzheimer's disease, Huntington's disease and Parkinson's disease;
neonatal brain damage in particular neonatal brain ischemia;
traumatic brain injury;
kidney ischemia;
hypoxia-ischemia (H-I) injuries;
stroke-like situations brain injuries;
heart ischemia;
myocardial infarction;
amyotrophic lateral sclerosis (ALS);
retinal damages;
ophthalmic diseases such as ischemic optic neuropathy and glaucoma;
skin damages;
sterile inflammatory diseases such as diabetes, atherosclerosis, cardiac ischemia, gout, pseudogout, joint loosening, atherosclerosis, syndromes triggered by aluminium salts, non-arteritic ischemic optic neuropathy (NAION), glaucoma, metabolic diseases;
non-sterile inflammatory diseases such as bacterial infection in particular with bacteria producing pore-forming toxins, influenza virus infection and single-stranded (ss) RNA Rhabdoviridae infection such as Maraba virus or vesicular stomatitis virus (VSV);
diseases caused by pathogenic bacteria, such as *Brucella, Staphylococcus aureus* and *Salmonella*;
obesity;
metabolic syndrome; and
nonalcoholic fatty liver disease.

More particularly, said diseases and/or injuries are selected from chronic degenerative diseases. Preferably they are chosen among Alzheimer's disease, Huntington's disease and Parkinson's disease, more specifically Alzheimer's disease.

According to yet another of its aspects, the invention is directed to a method for preventing and/or treating diseases and/or injuries in which Caspase-2 activity is implicated, comprising at least a step of administering to an individual in need thereof at least an effective amount of at least one compound in accordance with the invention, in which $R_2$ is as above defined.

According to another of its aspects, the present invention relates to a pharmaceutical composition comprising at least one compound according to the invention in which $R_2$ is as above defined, and at least one pharmaceutically acceptable excipient.

The pharmaceutical compositions of the invention may contain more particularly an effective dose of at least one compound according to the invention in which $R_2$ is as above defined.

An "effective dose" means an amount sufficient to induce a positive modification in the condition to be regulated or treated, but low enough to avoid serious side effects. An effective dose may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

A compound of formula (I) according to the invention in which R₂ is as above defined may be administered in an effective dose by any of the accepted modes of administration in the art.

In one embodiment, this compound may be used in a composition intended to be administrated by oral, nasal, sublingual, ophthalmic, topical, rectal, vaginal, urethral or parenteral injection route.

The route of administration and the galenic formulation will be adapted by one skilled in the art pursuant to the desired pharmaceutical effect.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

A medicament or pharmaceutical composition of the invention may be in the form of tablets, pills, powders, lozenges, sachets, cachets, elixirs, suspensions, emulsions, solutions, syrups, aerosols, sprays, ointments, gels, creams, sticks, lotions, pastes, soft and hard gelatine capsules, suppositories, sterile injectable solutions, sterile packages powders and the like.

According to one embodiment, a pharmaceutical composition of the invention may be intended to be administered separately, sequentially or simultaneously with an agent useful for the prevention and/or the treatment of a disease condition, in particular Alzheimer's disease, said agent being different from the compound of formula (I) of the invention.

b) Activity-Based Probe

The compounds of the present invention and more particularly the compounds for which the R₂ radical is selected from

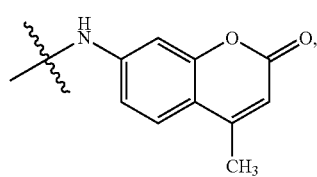

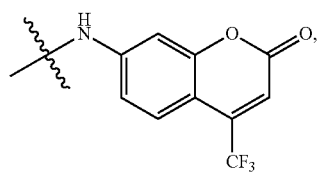

-continued

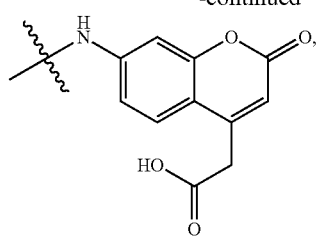

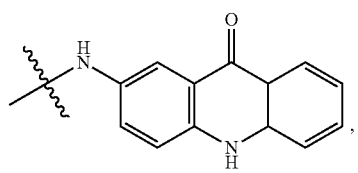

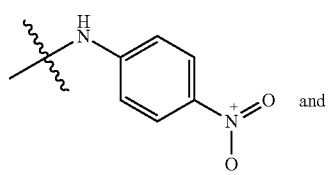

and

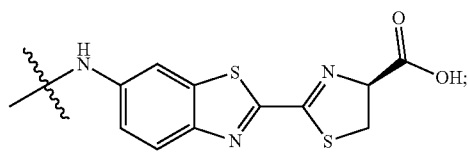

may be used as activity-based probe to selectively detect Caspase-2 activity.

Thus, according to one of its aspects, the present invention relates to the use of a compound according to the invention in which R₂ is as above defined, as activity-based probe (ABP) to selectively detect Caspase-2 activity.

The present invention will be better understood by referring to the following examples and FIG. 1 which are provided for illustrative purpose only and should not be interpreted as limiting in any manner the instant invention.

EXAMPLES

Example 1: Preparation of the Compound 2 According to the Invention

The synthesis of compound 2 according to the invention is inspired by the process of preparation of the compound TRP601 represented below:

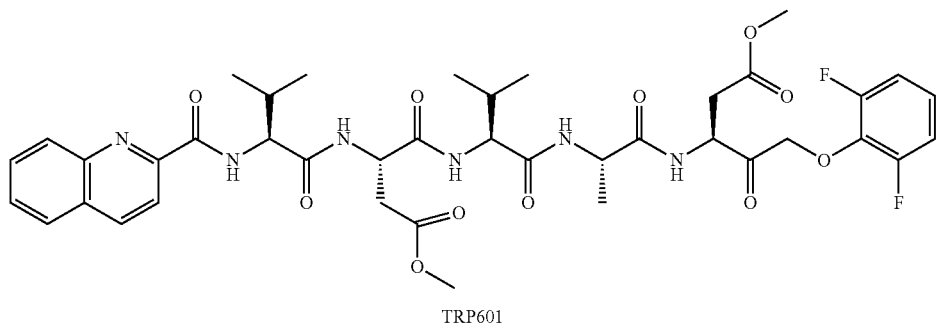 [SMILES: COC(=O)C[C@H](NC(=O)[C@H](C)NC(=O)[C@@H](NC(=O)[C@H](CC(=O)OC)NC(=O)[C@@H](NC(=O)c1ccc2ccccc2n1)C(C)C)C(C)C)C(=O)COc1c(F)cccc1F]
TRP601

The synthesis of TRP601 is described in D. Chauvier et al. Cell Death and Disease (2011) 2, e203.

Compound 2 of the present invention differs from TRP601 in that:

the $P_1$ and $P_4$ amino acid residues are represented by

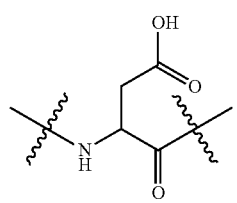 [SMILES: *NC(CC(=O)O)C(*)=O]

instead

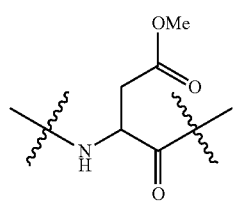 [SMILES: *NC(CC(=O)OC)C(*)=O]

in TRP601; and there is a

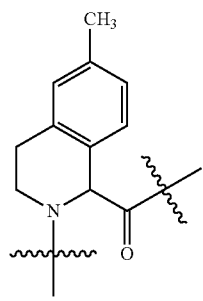 [SMILES: *C(=O)C1c2ccc(C)cc2CCN1*]

radical instead of

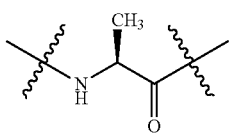 [SMILES: *N[C@@H](C)C(*)=O]

in TRP601.

The compound 2 has thus been obtained by reproducing the steps disclosed in the above mentioned article to lead to TRP601 except that:

the precursor

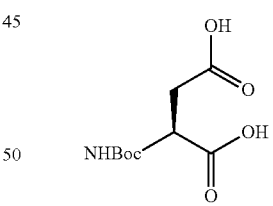

has been used instead of

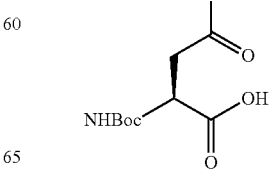

to introduce the P$_1$ and P$_4$ amino acid residues; and the precursor

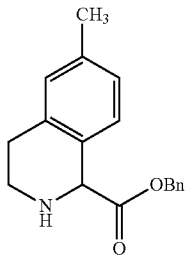 [SMILES: Cc1ccc2c(c1)CCNC2C(=O)OCc1ccccc1]

has been used instead of

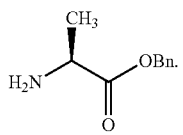

The precursor of the P$_1$ and P$_4$ amino acid residues has been prepared starting from the commercially available (S)-aspartic acid in which the amine function has been protected by a Boc group according to a well-known protocol for the skilled artisan.

The precursor of

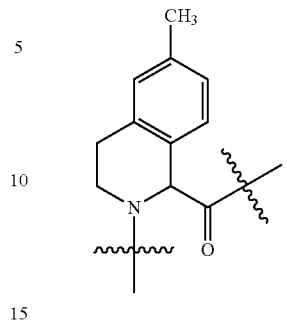

has been obtained according to Herdeis C Hubmann H Tetrahedron: Asymetry 1992, 3:1213 and X was obtained as described by Maillard et al., in Biooganic & Medicinal Chemistry 19 (2011):5833-5851.

The other building blocks of the compound 2 have been introduced in the same manner as for TRP601 in the above mentioned publications, i.e. with the same reagents, in the same conditions and with the same quantities.

Compound 2 has thus been obtained with a yield of more than 90% and characterized by HPLC.

Example 2: Caspase-2 and Caspase-3 Inhibition Assays (In Vitro)

The efficiency of the compound 2 of the invention to inhibit Caspase-2 and Caspase-3 has been evaluated by using the below explained protocol.

The efficiency of the comparative compound Δ2Me-TRP601, that is an already known group II Caspase inhibitor (inhibitor of Caspase-2, Caspase-3 and Caspase-7), has been assessed by a similar protocol described in Chauvier et al., 2011 Cell Death Dis 2011, 2:e203.

These two tested compounds are represented below:

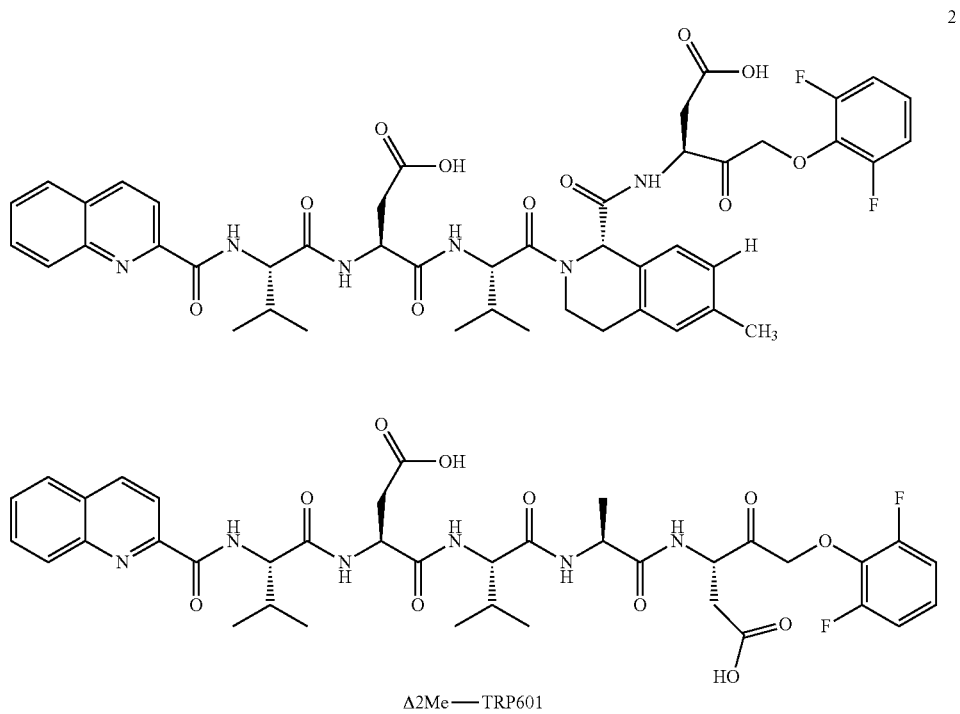

In this example, the Caspase-2 and Caspase-3 are human recombinant active enzymes that are respectively provided by Enzo Life® (ALX-201-057-U100) and R&D Systems® (707-C3-010/CF).

Caspase-2 is used at a final concentration of 0.1 nM in a "Caspase-2 buffer" containing 20 mM HEPES (pH 7.4), 5 mM DTT, 2 mM EDTA, 0.1% CHAPS and 800 mM succinate. Caspase-3 is used at a final concentration of 0.5 nM in a "Caspase-3 buffer" containing 20 mM HEPES (pH 7.4), 0.1% CHAPS, 5 mM DTT, and 2 mM EDTA.

The peptide substrates used for the enzymatic activity measurements are Ac-DEVD-AMC and Ac-VDVAD-AMC commercialized by EnzoLife® (respectively referenced ALX-260-031-M005 and ALX-260-060-M005). They are fluorogenic due to the presence of their AMC (7-amino-4-methylcoumarin) end group. The releasing of AMC enables to follow the enzymatic activity in fluorescence unit RFU over time in a 96-wells microplate (COSTAR 3915).

The fluorescence values are measured at 37° C. with a spectrofluorometer with a microplate reader BMG FLUOstar OPTIMA. This apparatus is driven by the software Biolise® and is equipped with thermoelectric cooling device by Peltier effect. The mathematic analysis of the experimental data are done with the software Kaleidagraph@.

The inhibitory properties of the tested compounds are evaluated by the determination of the $k_{inact}/K_I$ ratio regarding either Caspase-2 or Caspase-3 wherein:

$k_{inact}$ is the maximal inactivation rate constant, and $K_I$ is the dissociation constant according to:

$$E + I \underset{k_{-1}}{\overset{k_1}{\rightleftharpoons}} E \cdot I \xrightarrow{k_{inact}} \underset{\substack{complexe \\ covalent \\ inactif}}{E - I}$$

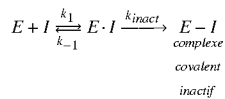

that reflects the inhibitor affinity regarding an enzyme.

Accordingly, the higher the ratio, the more efficient the inhibitor.

Said ratio is measured according to the continuous method (Allison R D. Curr Protoc Protein Sci. 2001 May; Chapter 3:Unit 3.5.; Chauvier et al., 2011 Cell Death Dis 2:e203; Tan et al., J Med Chem 2015, 58:598-312).

Briefly, Caspases activities were determined by monitoring the hydrolysis of fluorogenic substrates ($\lambda exc=355$ nm, $\lambda em=460$ nm) as a function of time, in the presence of untreated Caspases (control) or Caspases that had been incubated with a test compound, for 30 min minimum at 37° C. using a BMG Fluostar microplate reader (black 96-well microplates) and the initial velocity ($V_0$) was determined from the linear portion of the progress curve.

Substrates and compounds were previously dissolved in DMSO at 10 mM, with the final solvent concentration kept at lower 4% (v/v). $V_0$, relative velocities, $K_M$ and $IC_{50}$ were determined from experimental datas using Mars datas Analysis 2.0 and Kaleidagraph softwares.

For irreversible inhibitors, inactivation can be represented by the minimum kinetic scheme, where E and I are the free forms of enzyme and inhibitor, E*I a kinetic chimera of the Michaelis complex and E-I the covalent complex or inactivated enzyme.

$$E + I \rightleftharpoons E * I \xrightarrow{K_I \, k_3} E - I$$

Inhibitor binding affinity (dissociation constant, $K_I$) and first-order rate constant ($k_3$) parameters were determined for Caspase-2 and Caspase-3 using the progress curve method. The ratio $k_3/K_I$ was obtained by fitting the experimental data to the equations (F.U., fluorescence unit):

$$F.U. = \int_0^t v_i \, dt + F.U._0 \frac{-v_0 \times e^{-\pi * t}}{\pi} + F.U._0$$

$$\text{with } \pi = \frac{k_i \times [I]'}{K_I + [I]} \text{ and } [I]' = \frac{[I]}{1 + [S]/K_m}$$

Linear and nonlinear regression fits of the experimental data to the equations were performed with Kaleidagraph Software.

Determination of the $k_{inact}/K_I$ Ratio for the Caspase-2 and Caspase-3 Activity A continuous method of determination of the $k_{inact}/K_I$ ratio was used for evaluating the inhibitory activity of the tested compounds against Caspase-2 and Caspase-3.

The reaction mixture is prepared by letting the enzyme and the buffer incubate at 37° C.

The tested inhibitory compounds are prepared at different concentrations (¼ $IC_{50}$; ½ $IC_{50}$; $IC_{50}$; 2 $IC_{50}$; 4 $IC_{50}$) and put in the microplate.

For compound 2 according to the invention, the concentration used regarding the inhibition of:

Caspase-2 are 0; 0.1625; 0.3125; 0.625; 1.25 and 2.5 nM; and

Caspase-3 are 6.25; 12.5; 25; 50 and 100 nM.

For compound Δ2Me-TRP-601 (comparative compound), the concentration used regarding the inhibition of:

Caspase-2 are 0.15625; 0.3125; 0.625; 1.25 and 2.5 nM; and

Caspase-3 are 0.15625; 0.3125; 0.625; 1.25 and 2.5 nM.

Then the reaction mixture comprising the enzyme, the buffer and the substrate is rapidly added in the wells.

The activities of the enzyme are measured between 45 and 60 minutes.

The RFU (Relative Fluorescence Units)=f(times) curves are traced for each concentration of tested molecule according to the following equation:

$$((((-V_0)*(\exp(-k_{obs}*m0)))+V_0)/k_{obs}*)+RFU_0$$

in which:

$V_0$ corresponds to the initial rate (RFU$^{-1}$) in the concentration of 0 of the tested inhibitory compound;

$k_{obs}$ is the inactivation rate constant;

$RFU_0$ is the fluorescence value at t=0 min; and m0 is the variable i.e. the inhibitor concentration.

Adjusting the curve $f([I])=k_{obs}$ in an hyperbole using the Kaleigagraph software is then done in order to obtain the $k_{inact}/k_I$ ratio on the basis of the following equation:

$$K_{obs}=k_{inact}\times[I]/(K_I\times[I])$$

The so-obtained $k_{inact}/K_I$ ratios are reported in the following table.

| Inhibitor | Inactivation constant $k_{inact}/K_I(M^{-1}\cdot s^{-1})$ | |
| --- | --- | --- |
| | Caspase-2 | Caspase-3 |
| Compound 2 (compound according to the invention) | 1 760 857 | 30 514 |
| Δ2Me-TRP-601 (comparative compound) | 1 569 820 | 1 922 797 |

From this table it clearly appears that compound 2 is as efficient as Δ2Me-TRP601 to inhibit Caspase-2.

However, these two compounds react totally differently with respect to Caspase-3.

Indeed, compound 2 is 57 times more efficient to inactivate Caspase-2 than to inactivate Caspase-3.

It may be noticed that Δ2Me-TRP-601 does not exhibit this selectivity.

As a conclusion, compound 2 is not only efficient to inhibit Caspase-2, but is also selective regarding Caspase-2 with respect to Caspase-3.

Example 3: Protection Against Cellular Death Assay

In this example, the protective effect of the compound 2 of the invention against cellular death induced by vincristine (a vinca alkaloid) is tested using a well-known flow cytometry cell death assay based on propidium iodide staining.

a). Cellular Model

To evaluate the protecting effect of compound 2, a Caspase-dependent cellular model is used.

Human HeLa cells are used in this model. HeLa cells (cervical cancer cell line) were obtained from American Type Cell Collection (ATCC), and were cultured in Dulbecco's Modified Eagle Medium (DMEM, High Glucose, GlutaMAX™, Pyruvate) (Gibco, Life technologies), supplemented with 10% FCS and antibiotics (Gibco, Life technologies).

Human HeLa cells are treated with Vincristine (Sigma Aldrich) solubilized in water at 5 mM. Vincristine works partly by binding to the tubulin protein, stopping the cell from separating its chromosomes during the metaphase; the cell then undergoes apoptosis.

Propidium iodide (PI) (Sigma Aldrich) is used to evaluate plasma membrane permeabilisation, a sign of cell death.

b). Treatment and Marking Conditions 24 hours before pharmacological treatment, HeLa cells were plated into 24-well plates. Culture medium was then removed, cells were washed with PBS, and fresh medium containing compound 2 at different concentrations (3, 10, 30 and 60 μM) was added 1 hour before addition of vincristine. Cells were exposed or not (control), to 20 nM Vincristine for 48 hours.

The content of each well is collected (supernatant+ trypsinization's products) is added to PBS and then centrifuged (900 rpm; 5 min).

The pellet obtained is put into 300 μL of a medium comprising propidium iodide and incubated (37° C., 5% $CO_2$) in the dark for 5 minutes and then subjected to flow cytometry analysis.

c). Cells Analysis

The cells are then analyzed by flow cytometry with an excitation of 561 nm.

Fluorescence-Activated Cell Sorting was performed using a FACSCalibur cytometer (Becton Dickinson, San Jose, Calif.). For each sample, data from 5,000 Cells were registered and analyzed with the CellQuest Pro™ software (Becton Dickinson). Analysis included FSC (Forward Scatter/relating to the cells' size) and SSC (Side Scatter/relating to the cells' granularity) parameters together with FL-1 and FL-3 channel.

The concentrations of vincristine and of compound 2 are indicated in the following table for each treatment that has been applied to the cells.

| Treatment | Vincristine (nM) | Compound 2 (μM) |
| --- | --- | --- |
| Control | 0 | 0 |
| A | 20 | 0 |
| B | 20 | 3 |
| C | 20 | 10 |
| D | 20 | 30 |
| E | 20 | 60 |

The percentage of propidium iodide positive cells gives an estimation of cell death. The results are shown in FIG. 1 where histograms represent means of 3 independent experiments. Each experimental value corresponds to flow cytometry analysis of 5000 cells.

Control composition, which neither contains vincristine nor inhibitor, enables to estimate the quantity of cells that died naturally.

Composition A, which contains vincristine but no inhibitor, provides the total number of dead cells that corresponds to the sum of naturally dead cells and of apoptotic cells induced by vincristine.

It thus appears clearly from these results that compound 2 protects the cells against apoptotic death induced by vincristine in a dose-dependent manner.

The invention claimed is:

1. A compound of formula (I):

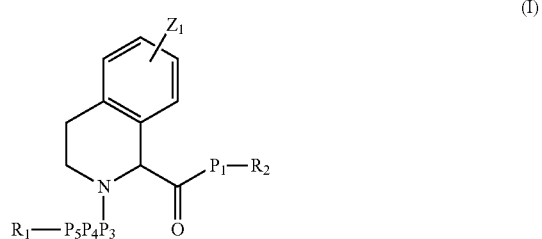

(I)

wherein:

$Z_1$ is a $(C_1\text{-}C_6)$alkyl group;

$P_5$ is selected from the following amino acid residues

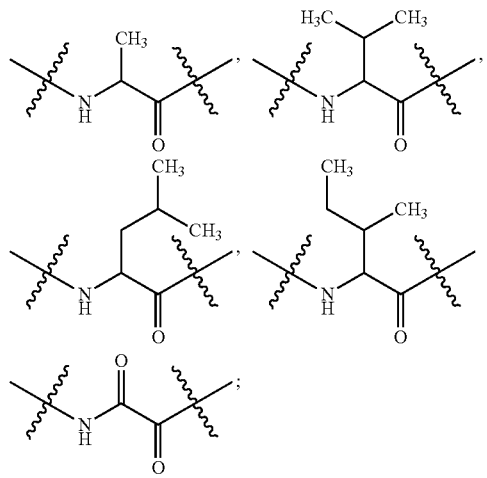

$P_1$ and $P_4$, identical or different, are selected from the following amino acid residues

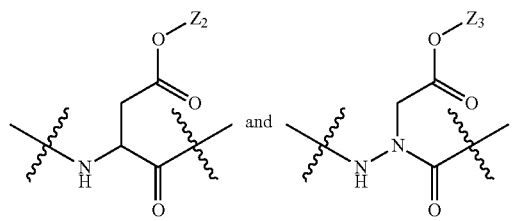

in which $Z_2$ and $Z_3$, identical or different, are selected from a hydrogen atom and a $(C_1\text{-}C_6)$alkyl group;

$P_3$ is selected from the following amino acids residues

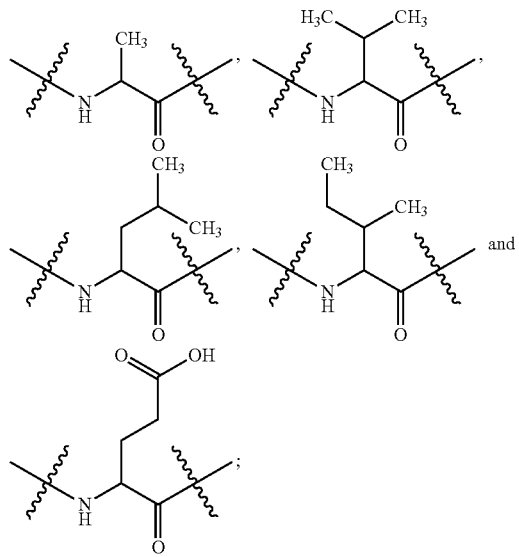

$R_1$ is selected from

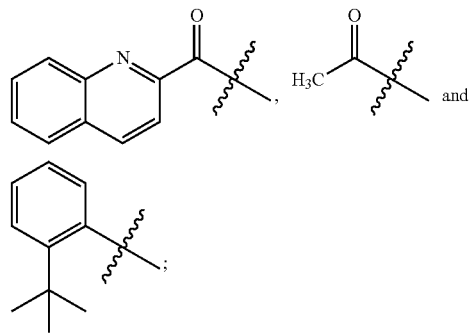

and $R_2$ is selected from

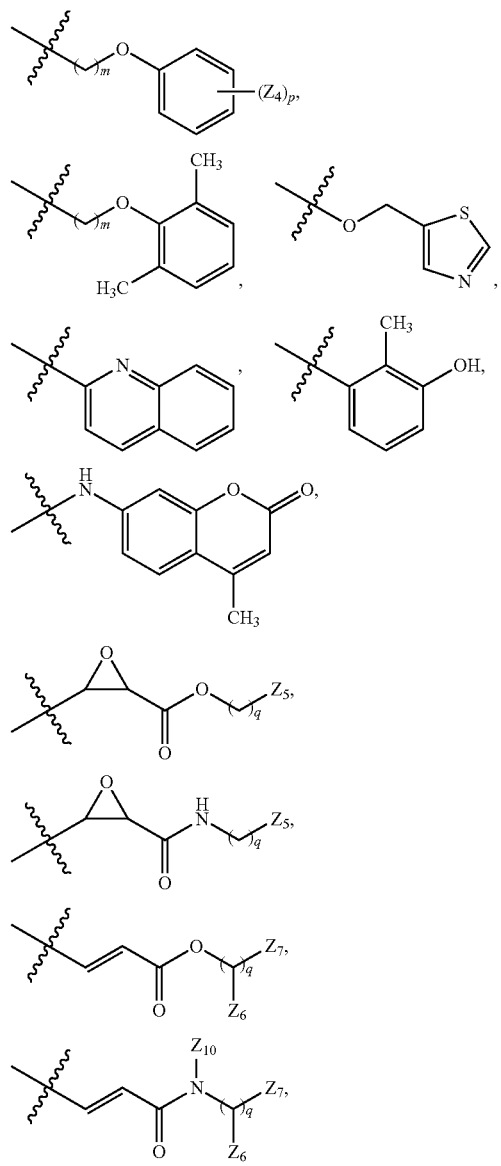

33

-continued

[chemical structures shown]

in which m is 0, 1 or 2;

p is 1, 2, 3 or 4;

$Z_4$ is a halogen atom;

q is 0 or 1;

$Z_5$ is selected from a $(C_1$-$C_6)$alkyl and a phenyl group, said phenyl group being substituted or not by an amino group;

$Z_6$, $Z_7$ and $Z_{10}$, identical or different, are selected from a hydrogen atom, a $(C_1$-$C_4)$alkyl, a tetrahydroquinolynyl and a —$(CH_2)_i$-aryl group with i being 0, 1 or 2, said aryl group being substituted or not by one, two, three, or four halogen atom(s) or one $(C_1$-$C_4)$ alkyl group; and $Z_8$ and $Z_9$, identical or different, are selected from a halogen atom and a $(C_1$-$C_6)$alkyl group;

or one of its salts;

said compound of formula (I) being in all the possible racemic, enantiomeric and diastereoisomeric isomer forms.

34

2. Compound according to claim 1 of formula (II):

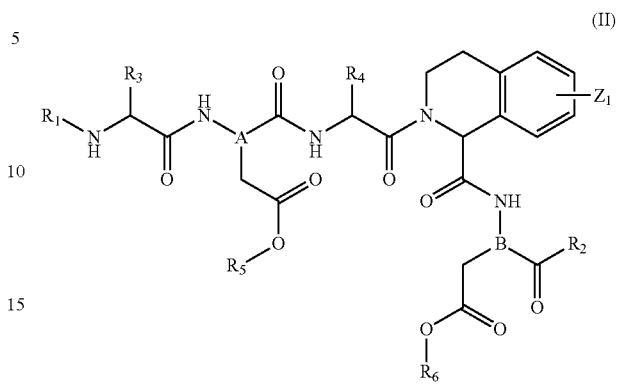

(II)

wherein:

$R_1$, $R_2$ and $Z_1$ are as defined in the formula (I) according to claim 1;

$R_3$ is selected from a —$CH_3$, a —$CH(CH_3)_2$, a —$CH_2CH(CH_3)_2$ and a —$CH(CH_3)CH_2CH_3$ group;

A and B, identical or different, are selected from a nitrogen atom and a —CH— group;

$R_5$ and $R_6$, identical or different, are selected from a hydrogen atom and a $(C_1$-$C_6)$alkyl group; and $R_4$ is selected from a —$CH_3$, a —$CH(CH_3)_2$, a —$CH_2CH(CH_3)_2$, a —$CH(CH_3)CH_2CH_3$ and a —$(CH_2)_2CO_2H$ group;

or one of its salts;

said compound of formula (II) being in all the possible racemic, enantiomeric and diastereoisomeric isomer forms.

3. Compound of formula (II) according to claim 2, wherein at least one of A and B is a —CH group.

4. Compound according to claim 1 of formula (III):

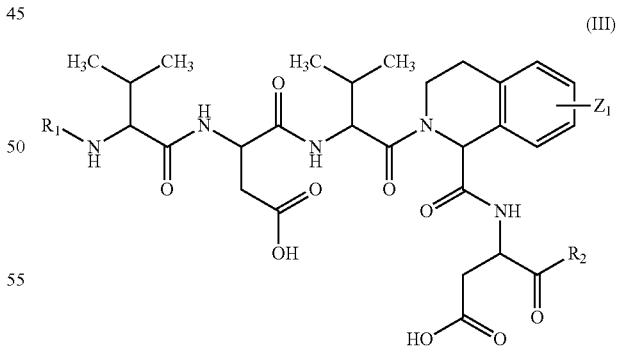

(III)

wherein $R_1$, $R_2$ and $Z_1$ are as defined in the formula (I) according to claim 1;

or one of its salts;

said compound of formula (III) being in all the possible racemic, enantiomeric and diastereoisomeric isomer forms.

5. Compound according to claim 1 of formula (IV):

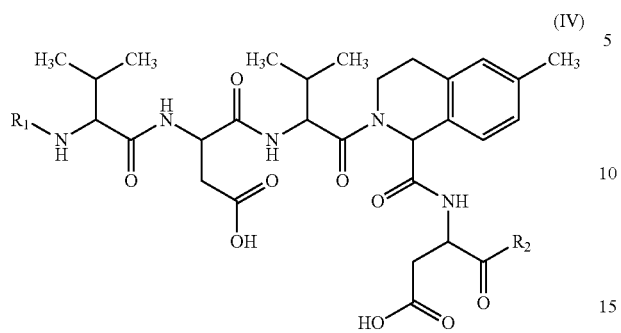

wherein $R_1$ and $R_2$ are as defined in the formula (I) according to claim 1;

or one of its salts;

said compound of formula (IV) being in all the possible racemic, enantiomeric and diastereoisomeric isomer forms.

6. Compound according to claim 1, wherein $R_1$ is

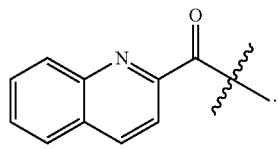 [SMILES: *C(=O)c1ccc2ccccc2n1]

7. Compound according to claim 1, wherein $R_2$ is selected from:

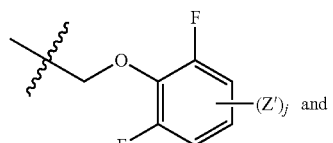

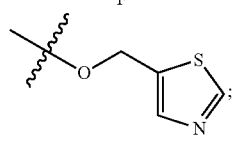

in which Z' is a fluorine atom and j is 0, 1 or 2.

8. Compound according to claim 1, having at least one asymmetric carbon atom of (S) configuration.

9. Compound according to claim 1, selected from:

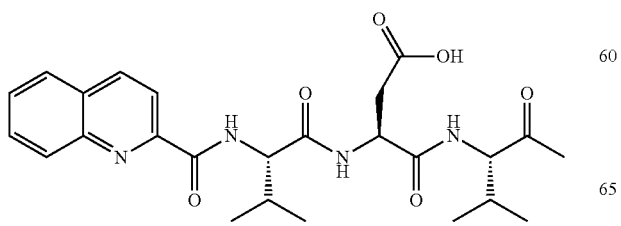

-continued

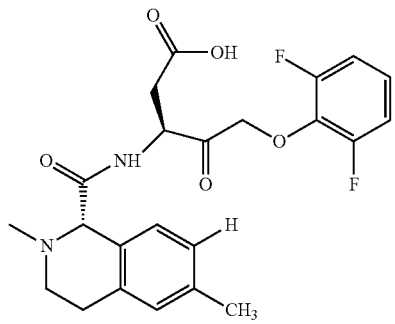

and

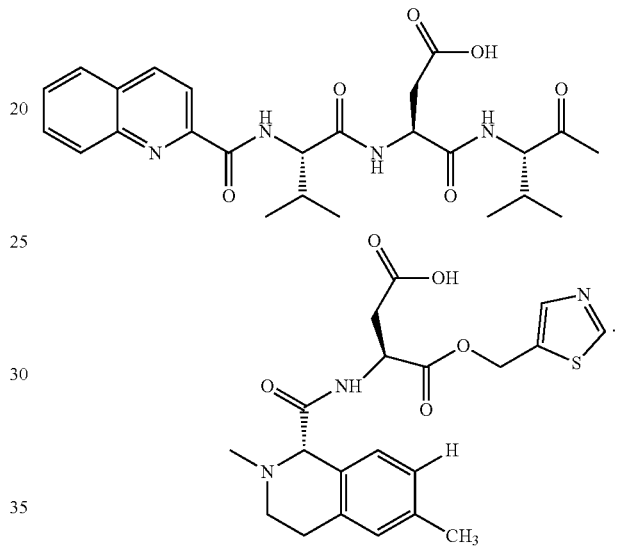

10. Compound according to claim 1, for its use as selective Caspase-2 inhibitor.

11. Pharmaceutical composition, comprising at least one compound according to claim 1 and at least one pharmaceutically acceptable excipient, wherein $R_2$ is selected from

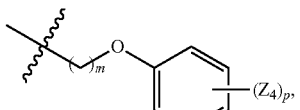

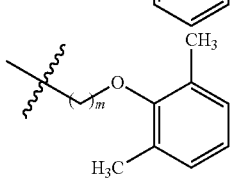 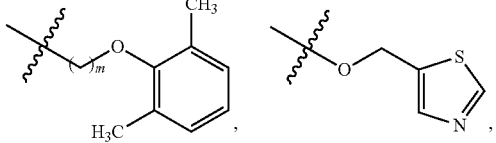

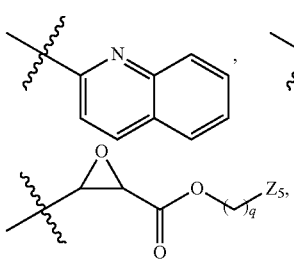 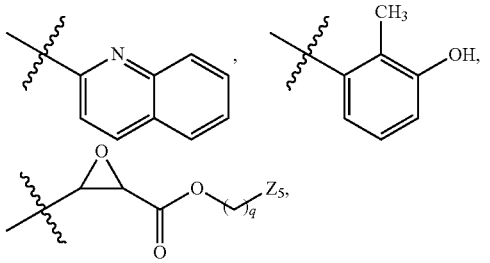

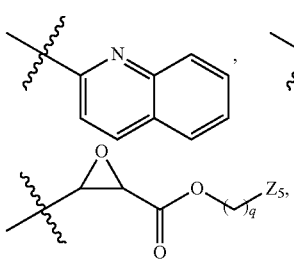

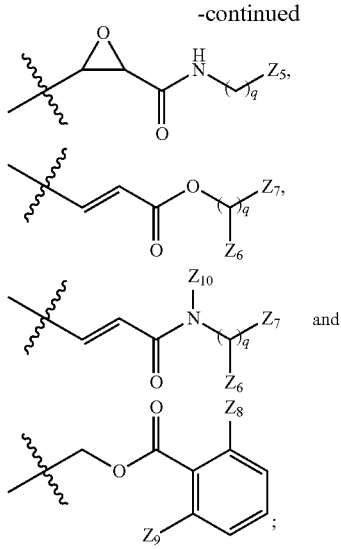

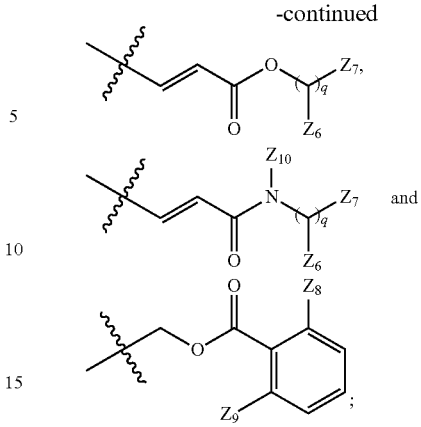

in which m, p, q, $Z_4$, $Z_5$, $Z_6$, $Z_7$, $Z_8$, $Z_9$ and $Z_{10}$ are as defined in the formula (I) according to claim 1.

12. Method for selectively inhibiting caspase-2 activity in a subject in need thereof, comprising the administration to said subject of a compound according to claim 1, wherein $R_2$ is selected from

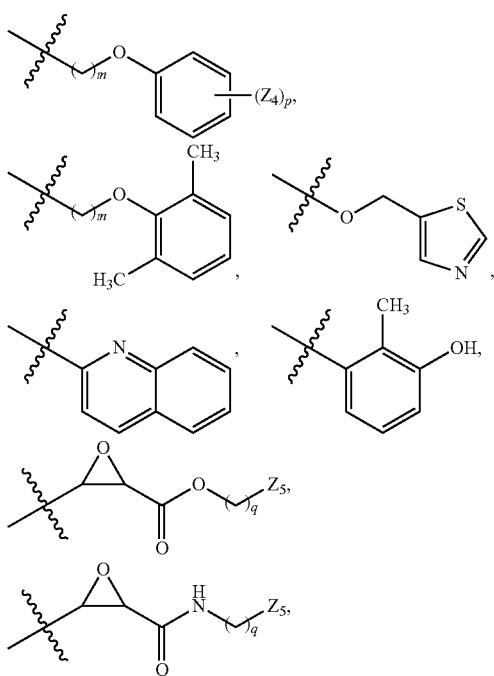

in which m, p, q, $Z_4$, $Z_5$, $Z_6$, $Z_7$, $Z_8$, $Z_9$ and $Z_{10}$ are as defined in the formula (I) according to claim 1.

13. Method according to claim 12 for inhibiting caspase-2 mediated cell death in said subject.

14. Method according to claim 12 for treating neonatal brain damage, ischemic brain injuries, ischemic optic neuropathy, glaucoma.

15. Method according to claim 12 for treating metabolic syndrome, nonalcoholic fatty liver disease, or obesity, in said subject.

16. Method according to claim 12 for inducing a neuroprotection in said subject.

17. Method according to claim 12 for inducing a neuroprotection in said subject, wherein the subject is suffering from Alzheimer's disease, Huntington's disease, or Parkinson's disease.

18. Method according to claim 12 for inducing a neuroprotection in said subject, wherein the subject is suffering from neonatal brain damage, traumatic brain injury, stroke-like situations, brain injuries, ischemic optic neuropathy, or glaucoma.

19. Method according to claim 12 for inhibiting neurodegeneration in said subject.

20. Method according to claim 12, for inhibiting neurodegeneration in a subject suffering from Alzheimer's disease, Huntington's disease, or Parkinson's disease.

21. Method according to claim 12 for treating cognitive decline in said subject, wherein the subject is suffering from Alzheimer's disease.

22. Method according to claim 12 for protecting neuronal cells from Amyloid beta peptides and/or Amyloid-beta oligomers toxicity, wherein the subject is suffering from Alzheimer's disease.

23. Method according to claim 12, for treating obesity, metabolic syndrome, or nonalcoholic fatty liver disease.

* * * * *